(12) United States Patent
Im (10) Patent No.: US 9,307,973 B2
(45) Date of Patent: Apr. 12, 2016

(54) MUSCLE RETRACTOR FOR SPINE SURGERY

(71) Applicant: SOONCHUNHYANG UNIVERSITY INDUSTRY ACADEMY COOPERATION FOUNDATION, Asan-si, Chungcheongnam-do (KR)

(72) Inventor: Soo-Bin Im, Bucheon-si (KR)

(73) Assignee: SOONCHUNHYANG UNIVERSITY INDUSTRY ACADEMY COOPERATION FOUNDATION, Chungcheongnam-Do (KR)

(*) Notice: Subject to any disclaimer, the term of this patent is extended or adjusted under 35 U.S.C. 154(b) by 390 days.

(21) Appl. No.: 13/901,539

(22) Filed: May 23, 2013

(65) Prior Publication Data

US 2014/0221761 A1 Aug. 7, 2014

(30) Foreign Application Priority Data

Feb. 4, 2013 (KR) ........................ 10-2013-0012202

(51) Int. Cl.
*A61B 17/02* (2006.01)

(52) U.S. Cl.
CPC ............. *A61B 17/0206* (2013.01); *A61B 17/02* (2013.01); *A61B 17/025* (2013.01)

(58) Field of Classification Search
CPC .. A61B 17/02; A61B 17/0206; A61B 17/025; A61B 2017/0256–2017/0262

USPC ................................................. 606/54–59, 90
See application file for complete search history.

(56) References Cited

U.S. PATENT DOCUMENTS

| 4,604,995 A | 8/1986 | Stephens et al. |
| 5,908,382 A * | 6/1999 | Koros ............... A61B 17/0206 600/215 |
| 2008/0140202 A1 | 6/2008 | Allard et al. |
| 2009/0112266 A1 | 4/2009 | Weng et al. |
| 2014/0058210 A1 | 2/2014 | Raymond et al. |

FOREIGN PATENT DOCUMENTS

| CN | 1913834 A | 2/2007 |
| KR | 10-2011-0094891 A | 8/2008 |

* cited by examiner

*Primary Examiner* — Nicholas Plionis
(74) *Attorney, Agent, or Firm* — Revolution IP, PLLC (57) ABSTRACT

Provided is a muscle retractor for spine surgery including: first and second retractors having blades configured to support a spine and muscles, and insertion blocks extending from the blades and having facing open surfaces; an expander having expansion arms slidably inserted into the insertion blocks of the first and second retractors, a gear rack movably installed at both of the expansion arms and having a gear section formed at one surface thereof, and a ratchet installed at the expansion arm moving along the gear rack and locked to or released from the gear section of the gear rack; a slider accessibly inserted into the blade of the first retractor or the second retractor in a projected state; and an auxiliary plate pivotally installed at a lower portion of the blade of the first retractor of the first and second retractors supporting the muscles.

4 Claims, 7 Drawing Sheets

MUSCLE RETRACTOR FOR SPINE SURGERY

CROSS REFERENCE TO PRIOR APPLICATIONS

This application claims priority under 35 U.S.C. §119 to Korean Patent Application No. 10-2013-0012202, filed on Feb. 4, 2013, which is hereby incorporated by reference in its entirety.

BACKGROUND

1. Field of the Invention

The present invention relates to a muscle retractor for spine surgery, and more particularly, to a muscle retractor for spine surgery capable of retracting and spreading muscles around a spine during spine surgery.

2. Discussion of Related Art

In recent times, as people spend more time seated, patients with spine conditions due to incorrect posture or injury from a fall such as a lumbar herniated intervertebral disc (also known as a slipped disc) or the like are increasing.

When a spinal abnormality occurs, the spinal abnormality can be initially treated through drug treatment, exercise therapy, injection therapy, physical therapy, or the like. However, when symptoms of the spinal abnormality are severe, surgery of removing a herniated intervertebral disc or inserting a space configured to maintain a gap between vertebral bodies is performed.

Here, the spine surgery is performed through hemilaminectomy. For this, various types of retractors have been developed such that an operator can secure a visual field for a surgical area and smoothly insert a surgical instrument into a human body to perform a surgical procedure.

In an initial stage of the spine surgery, a retractor, which is manually operated, has been used to retract muscles. However, pulling power differs from individual to individual, and it is difficult for an assistant to concentrate only on a pulling action. For this reason, a self retractor that can more effectively spread muscles has been developed. Such a self retractor is constituted by a blade section in contact with muscles, and a retraction section configured to spread the muscles. While both of the sections are integrally formed with each other at the initial stage, the integrated blade cannot be easily inserted at a tilted angle or cannot be easily inserted into a narrow gap of two muscles strip, and a depth of back muscles differs from individual to individual. Accordingly, a self retractor having two sections, which are separated from each other before insertion and then coupled to each other after insertion into muscles to exchange various blades having different lengths with each other, has been developed.

Here, in such a self retractor, a lower end of the blade section is bent at an appropriate angle and length to stably surround and grip the muscles without slipping of the blade upon retraction of the muscles. However, the bent portion may interfere with the surroundings of the muscles and disturb insertion thereinto when the blade is inserted between the muscles.

In addition, in the conventional self retractor, the blade section in contact with the muscles should be coupled to the retraction section after the blade section is mounted on the muscles. In the related art, a cylindrical projection is formed at an upper end of the blade and a groove corresponding thereto is formed in the retraction section so that the retraction section is lowered and the blade is inserted thereinto. However, such a coupling process is not smooth and the blade is coupled to the retracting section under condition of applying a raising power to the blade. In connection with this, the blade gripping the muscles at an appropriate position in an initial stage may lose its grip of the muscles during the coupling process. For this reason, the self retractor should be installed again several times or the muscles blocking the operator's view should be cut out.

In addition, since the conventional self retractor must insert two blades between the muscles one by one, in order to insert the first blade between the muscles and then insert the second blade therebetween, the assistant must securely grip the first blade with no movement. However, since a position of the first blade is likely to be varied while the second blade is inserted even when the assistant securely grips the first blade, an insertion process of the blades becomes very complicated.

SUMMARY OF THE INVENTION

The present invention is directed to provide a muscle retractor for spine surgery capable of uniformly retracting muscles around a spine with a convenient coupling procedure and securing a surgical space and view by proper grip of muscle during spine surgery.

According to an aspect of the present invention, there is provided a muscle retractor for spine surgery for retracting muscles from a spine, including: first and second retractors having blades configured to support a spine and muscles, and insertion blocks extending from the blades and having facing open surfaces; an expander having expansion arms slidably inserted into the insertion blocks of the first and second retractors to expand the first and second retractors, a gear rack movably installed at both of the expansion arms and having a gear section formed at one surface thereof, and a ratchet installed at the expansion arm moving along the gear rack and locked to or released from the gear section of the gear rack; a slider accessibly inserted into the blade of the first retractor or the second retractor in a projected state and configured to restrict or release the corresponding retractor according to access thereof; and an auxiliary plate pivotally installed at a lower portion of the blade of the first retractor of the first and second retractors supporting the muscles, and pivoted according to insertion of the expansion arm of the expander into the insertion block of the first retractor and expanded while surrounding and gripping the muscles.

In addition, side surface grooves may be formed in both side surfaces of the blade of the first retractor, side surface grooves may also be formed at both side surfaces of the blade of the second retractor opposite to the side surface grooves, the slider may be accessibly inserted into one side surface groove of the side surface grooves of the first and second retractors in a projected state, and the projected portion of the slider may be inserted into the corresponding side surface groove to restrict the first and second retractors.

Further, a downwardly inclined groove may be formed in the side surface groove into which the slider is accessibly inserted, an inclined protrusion inserted into the inclined groove may protrude from the slider, and a resilient member configured to resiliently support the inclined protrusion may be installed between the inclined groove and the inclined protrusion.

A pivot unit of the auxiliary plate may include a pivot plate pivoted according to insertion of the expansion arm of the expander into an inner side surface of the insertion block of the first retractor; a movable block locked by the pivot plate and movable in the insertion block by the expansion arm as the locking is released upon pivotal movement of the pivot plate; a first link pivotally coupled to and interlocked with the movable block; a pivot link pivotally coupled to the first link and interlocked and pivoted about a pivot shaft of the first retractor by the first link; and a second link pivotally coupled to the pivot link and connected to the auxiliary plate to pivot the auxiliary plate in a forward or rearward direction.

Further, a projection configured to come in contact with the expansion arm inserted into the insertion block and pivot the pivot plate may protrude from a lower surface of the pivot plate, a resilient member may be installed at an inner side surface of the insertion block on the pivot plate, and a support member may be resiliently supported by the resilient member and comes in contact with an upper surface of the pivot plate to return the pivot plate to its original state.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

FIGS. 1 to 9 show a muscle retractor for spine surgery according to the present invention and components thereof.

Figure 1:
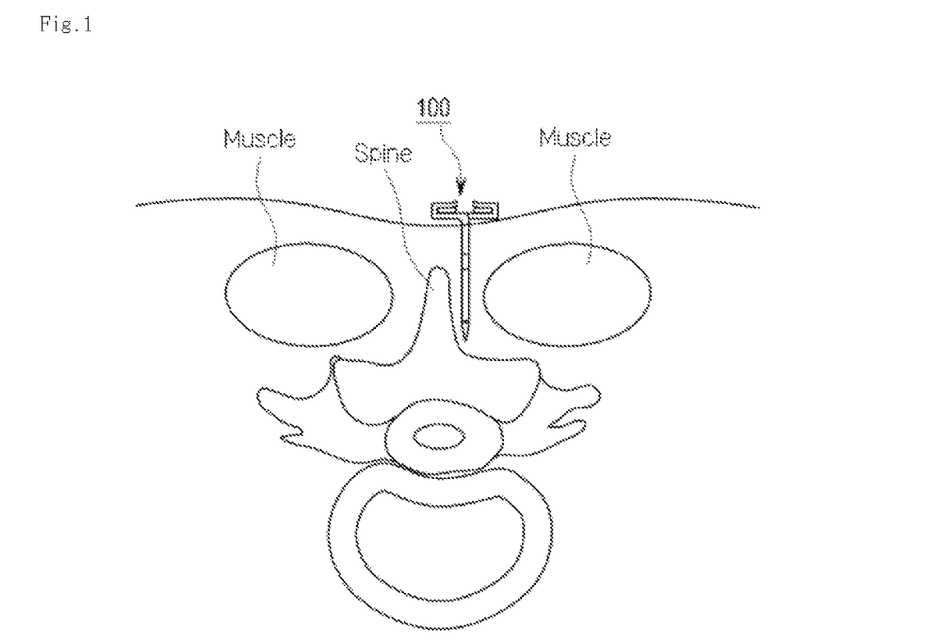
FIG. 1 is a view showing a surgical area to which a muscle retractor for spine surgery of the present invention is applied.

As shown in FIG. 1, a muscle retractor for spine surgery 100 of the present invention is an apparatus inserted between a spine and muscles around the spine to retract the muscles from the spine.

Figure 2:
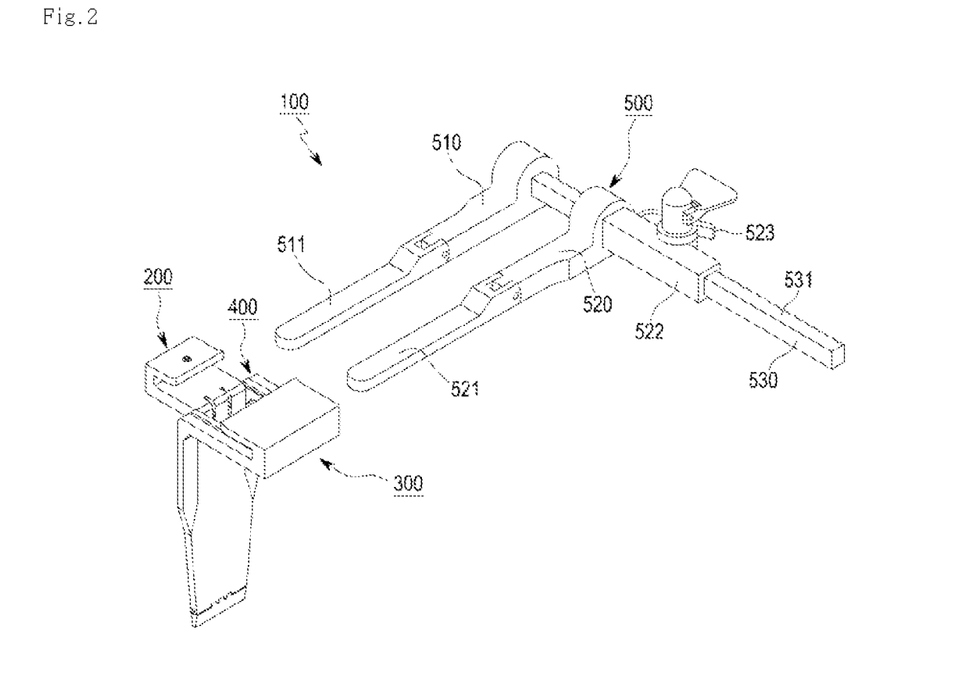
FIG. 2 is a configuration view of the muscle retractor according to the present invention.

As shown in FIG. 2, the muscle retractor for spine surgery 100 includes a pair of retractors 200 and 300, a slider 400, an expander 500, and so on.

Figure 3:
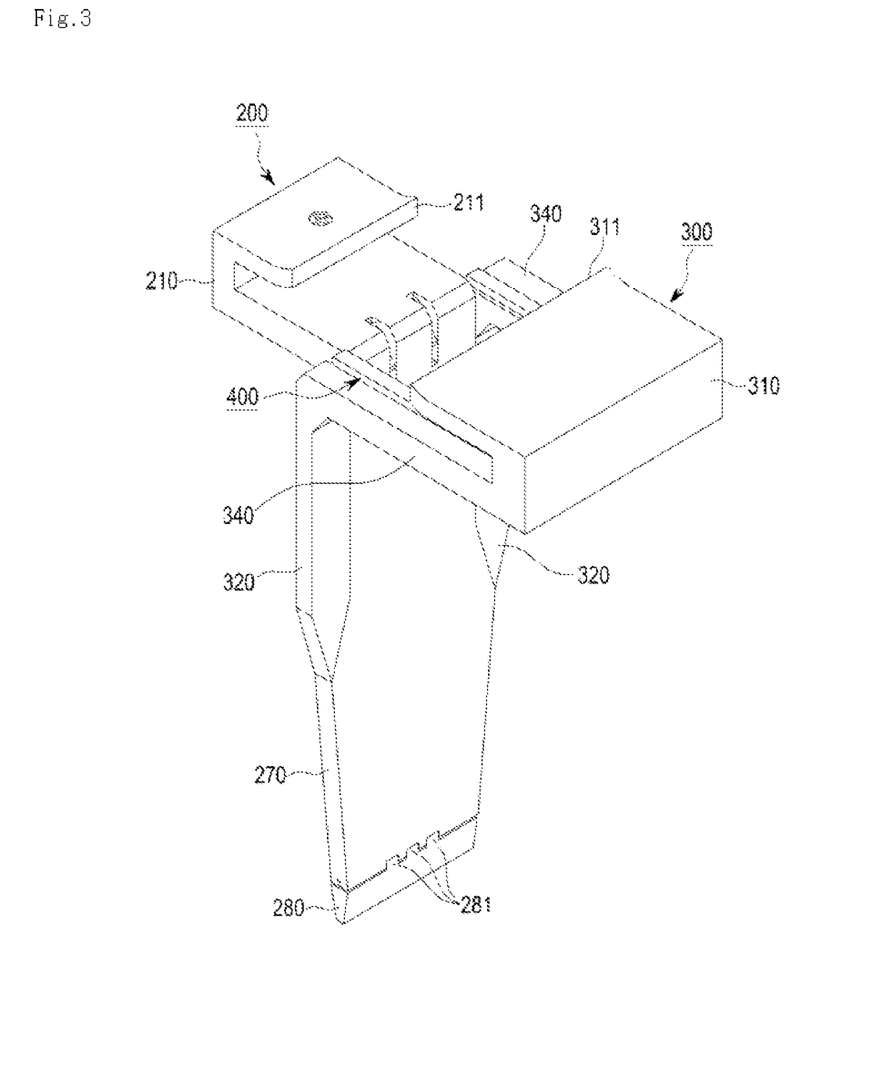
FIG. 3 is a view showing retractors constituting the muscle retractor according to the present invention.
Figure 4:
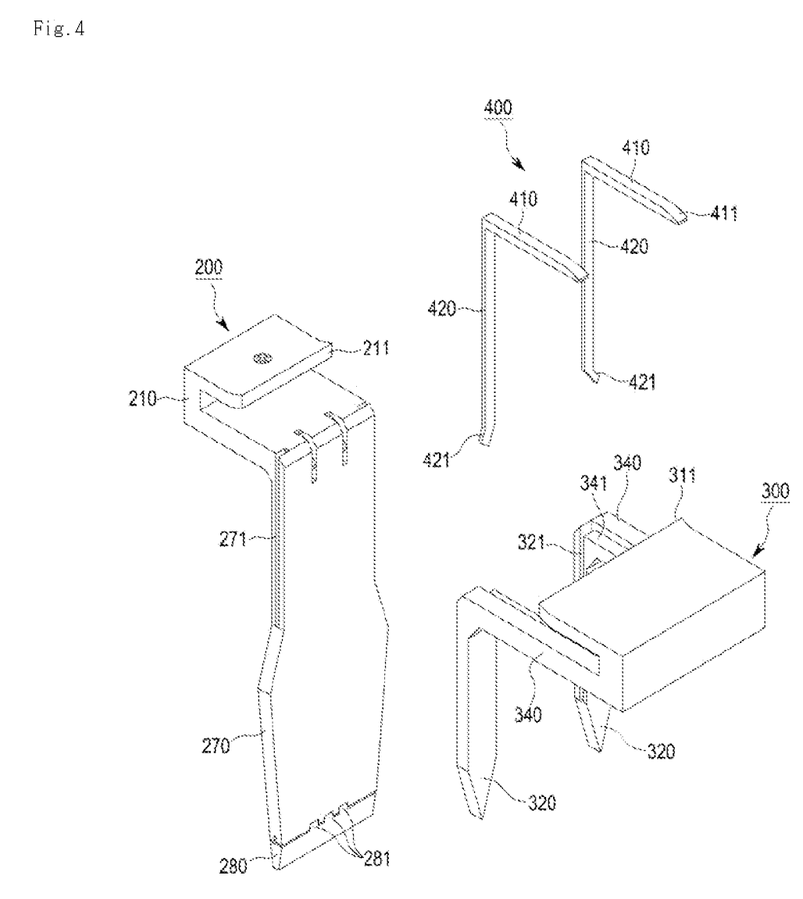
FIG. 4 is an exploded perspective view of the retractors according to the present invention.

As shown in FIGS. 2 to 4, the retractors 200 and 300 are constituted by a first retractor 200 and a second retractor 300, the first retractor 200 is an apparatus for retracting muscles around the spine, and the second retractor 300 is an apparatus supported by the spine.

The first retractor 200 includes a first insertion block 210 into which a first expansion arm 511 of the expander 500 (to be described below) is inserted, and a plate-shaped retraction blade 270 vertically extending downward from the first insertion block 210.

The first insertion block 210 has a substantially C-shaped cross section, a surface (a surface facing a second insertion block 310 of the second retractor 300 to be described below) of which is opened, an upper open end is formed as a curved end 211 gently bent upward and outward, and the plate-shaped retraction blade 270 extends downward from a lower open end thereof.

In addition, a pivot plate 220 having one hinged end is installed at an inner upper surface of the first insertion block 210, and the pivot plate 220 is pivoted about the hinge section at the inner upper surface of the first insertion block 210.

A resilient member 213 is installed at an inner surface of the first insertion block 210 of an upper portion of the pivot plate 220, and a support member 212 is installed to be resiliently supported by a lower portion of the resilient member 213 to come in contact with an upper surface of the pivot plate 220. The support member 212 is raised by the pivot plate 220 while compressing the resilient member 213, and then lowered by a resilient force of the resilient member 213 when an external force (the first expansion arm 511 of the expander 500 to be described below), which pivots the pivot plate 220, is released, pivoting the pivot plate 220 in a reverse direction (pivoting it in a downward direction).

Here, while the resilient member 213 may be any member having a resilient force, a compression coil spring may be provided as the resilient member. In addition, while the support member 212 may also be any member capable of pressing the pivot plate 220, a ball may be provided to minimize a frictional force with the pivot plate 220.

In addition, a projection 222 is formed at a lower surface of the pivot plate 220 such that the pivot plate 220 is rapidly pivoted as the first expansion arm 511 of the expander 500 (to be described below) is inserted into the first insertion block 210. The projection 222 may have a gently projecting shape.

Meanwhile, a movable block 230 is movably installed under the pivot plate 220 in the first insertion block 210, and a latching protrusion 231 protrudes from an upper surface of the movable block 230.

A latching groove 221 into which the latching protrusion 231 is inserted and latched is formed in a lower surface of the pivot plate 220 to correspond to the latching protrusion 231 of the movable block 230. Accordingly, the movable block 230 is restricted and fixed by the pivot plate 220 through coupling of the latching protrusion 231 and the latching groove 221, and then released from the pivot plate 220 to be in a movable state while the pivot plate 220 is pivoted upward.

In addition, a link unit connected to the movable block 230 to pivot an auxiliary plate 280 (to be described below) in forward and rearward directions is installed at the first retractor 200.

Figure 8:
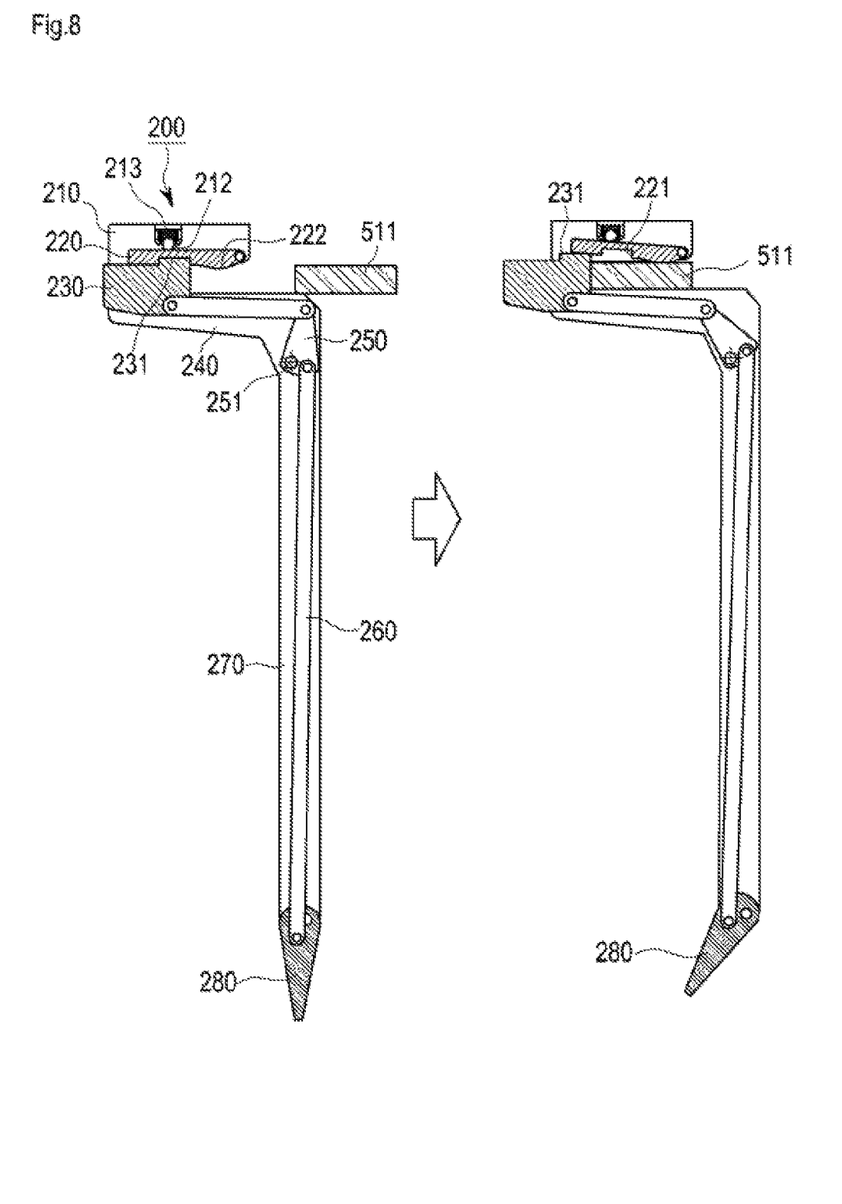
FIG. 8 is a view sequentially showing states before and after an expansion arm is inserted into the first retractor of the retractors according to the present invention.

As shown in FIG. 8, the link unit includes a bar-shaped first link 240 having one end pivotally coupled or hinged to one side of the movable block 230, a pivot link 250 having one side pivotally coupled to the other end of the first link 240, and a second link 260 having one end pivotally coupled to the other side of the pivot link 250 and the other end pivotally connected to the auxiliary plate 280 (to be described below).

Here, the pivot link 250 has a substantially triangular shape, a pivot shaft 251 installed at the first retractor 200 is pivotally coupled between both of hinge parts to which the first and second links 240 and 260 are hinged, and the pivot link 250 is pivoted about the pivot shaft 251.

Accordingly, the first link 240 is pulled according to movement of the movable block 230, the pivot link 250 is pivoted counterclockwise about the pivot shaft 251 by the first link 240, the second link 260 is pulled upward according to pivotal movement of the pivot link 250, and thus the auxiliary plate 280 is pulled and pivoted upward (see a right drawing of FIG. 8).

Meanwhile, the auxiliary plate 280 pivoted as described above is pivoted to an angle of 25 to 30 degrees.

The retraction blade 270 has a plate shape vertically extending downward from the lower open end of the first insertion block 210.

Side surface grooves 271 into which projected portions of the sliders 400 are inserted and latched are formed at both side surfaces of the retraction blade 270.

In addition, the auxiliary plate 280 is installed at a lower end of the retraction blade 270. The auxiliary plate 280 is pivotally installed at the lower end of the retraction blade 270 through a plurality of hinge protrusions 281 formed at an upper end thereof. That is, in the embodiment, three hinge protrusions 281 are exemplarily shown. Two hinge protrusions 281 disposed at both sides thereof are pivotally hinged to the retraction blade 270, and a lower end of the second link 260 is pivotally connected to the hinge protrusion 281 disposed at a center thereof.

Accordingly, since auxiliary plate 280 is pivoted by the above-mentioned link unit constituted by the first and second links 240 and 260 and the pivot link 250 and retracts the muscles around the spine in a pivoted state, damage to the muscles, which may be caused upon retraction, can be prevented.

The second retractor 300 corresponding to the first retractor 200 includes the second insertion block 310 into which a second expansion arm 521 of the expander 500 (to be described below) is inserted, and a pair of support blades 320 vertically extending downward from the second insertion block 310.

The second insertion block 310 has a substantially C-shaped cross-section having a surface facing the first insertion block 210 of the first retractor 200, which is open, an upper open end is formed as a curved end 311 gently bent upward and outward, extension sections 340 horizontally protrude from both sides of a lower open end, and the support blades 320 vertically extend downward from ends of the extension sections 340.

Meanwhile, the curved ends 211 and 311 formed at the first and second insertion blocks 210 and 310 of the first and second retractors 200 and 300 guide the first and second expansion arms 511 and 521 to be easily inserted into the first and second insertion blocks 210 and 310.

In addition, the support blades 320 of the second retractor 300 are blades configured to support the spine, and vertically extend downward from the extension sections 340 formed at both side ends of the second insertion block 310.

The extension sections 340 horizontally protrude from both side ends of the second insertion block 310, and stepped sections 341 in communication with side surface grooves 321 of the support blade 320 (to be described below) are formed in an inner end of the upper surface.

Meanwhile, the support blades 320 vertically protrude downward from ends of both of the extension sections 340, and the retraction blade 270 of the first retractor 200 is disposed between both of the support blades 320 to come in contact with both of the support blades 320.

In addition, the side surface grooves 321 into which the sliders 400 (to be described below) are inserted are formed at both side surfaces of the support blades 320, an upper end of the side surface groove 321 is configured to come in communication with the stepped section 341 of the extension section 340, inclined grooves 322 inclined downward toward a center portion of the support blade 320 are formed at lower portions of the side surface grooves 321, and the resilient members 330 configured to resiliently support the sliders 400 are installed in the inclined grooves 322.

Here, while the resilient member 330 may be any member that can resiliently support the slider 400, a compression coil spring may also be provided like the above-mentioned resilient member 213.

Projected one sides of the sliders 400 are inserted into the side surface grooves 321 formed at both side surfaces of the support blade 320 of the second retractor 300 to be accessibly installed, and a corresponding reactor, i.e., the first retractor 200, is restricted by or released from the second retractor 300 according to access of the sliders 400.

The slider 400 having a "⏋" shape includes a horizontal section 410 disposed at the stepped section 341 of the extension section 340, and a vertical section 420 vertically extending downward from one end of the horizontal section 410 and inserted into the side surface groove 321 of the support blade 320.

Meanwhile, an end of the horizontal section 410 is formed as a tip section 411 having a sharp tip, and an inclined protrusion 421 bent to correspond to the inclined groove 322 of the side surface groove 321 protrudes from a lower end of the vertical section 420 of the slider 400. Accordingly, as the inclined protrusion 421 is resiliently supported by a resilient member 330 in the inclined groove 322, one side of the slider 400 protrudes from the side surface groove 321 and the stepped section 341 by the resilient force of the resilient member 330.

Here, one projected portion of the vertical section 420 of the slider 400 is inserted into the side surface groove 321 formed in the retraction blade 270 of the first retractor 200 in a state in which it is inserted into the side surface groove 321 of the support blade 320, and thus the first and second retractors 200 and 300 are restricted by and coupled to each other.

Figure 9:
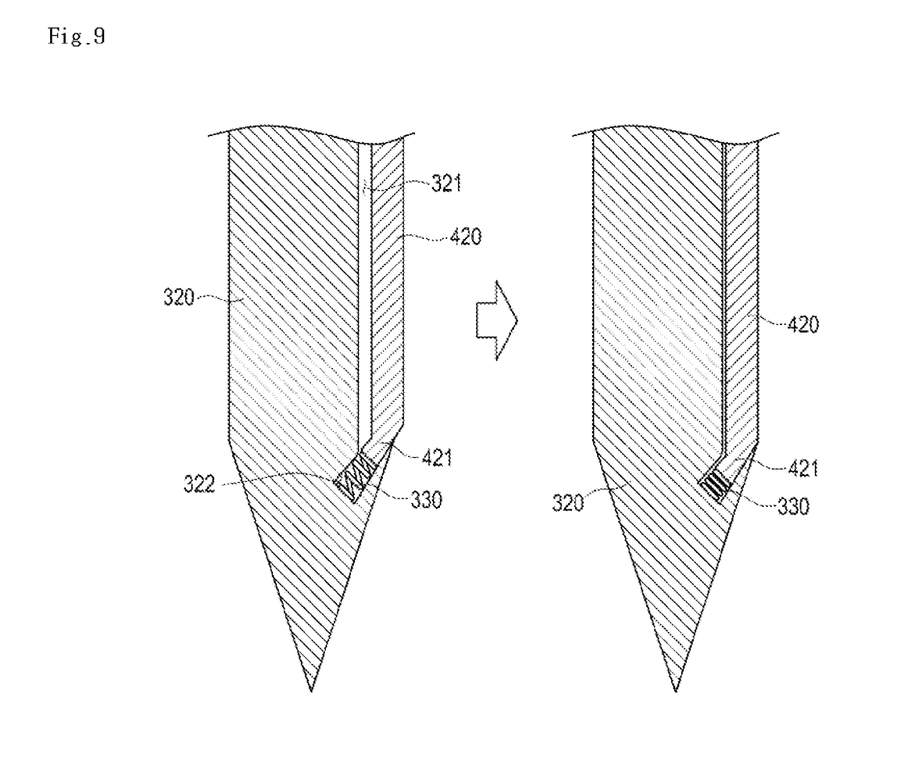
FIG. 9 is a view sequentially showing coupling and operating states of a slider with respect to the second retractor according to the present invention.

Then, when the horizontal section 410 of the slider 400 protruding over the extension section 340 is pushed by the second expansion arm 521 of the expander 500 (to be described below), the horizontal section 410 of the slider 400 is inserted into the stepped section 341 of the extension section 340, and as shown in FIG. 9, the vertical section 420 is completely inserted into the side surface groove 321 of the support blade 320 while compressing the resilient member 330. Accordingly, the first retractor 200 restricted by the slider 400 is released simultaneously with the slider 400 being separated from the side surface groove 271 of the retraction blade 270, and thus the first retractor 200 and the second retractor 300 become separable.

Meanwhile, as shown in FIGS. 7(a) to 7(c), in coupling of the first and second retractors 200 and 300 by the slider 400, in a state in which the slider 400 is inserted into the side surface groove 321 of the second retractor 300, after the projected portion of the slider 400 projected by the resilient member 330 at the side surface groove 321 of the second retractor 300 coincides with an upper portion of the side surface groove 271 of the first retractor 200, when the second retractor 300 and the first retractor 200 are vertically coupled to each other, the projected portion of the slider 400 is inserted into the side surface groove 271 of the first retractor 200 to couple the first and second retractors 200 and 300.

Figure 5:
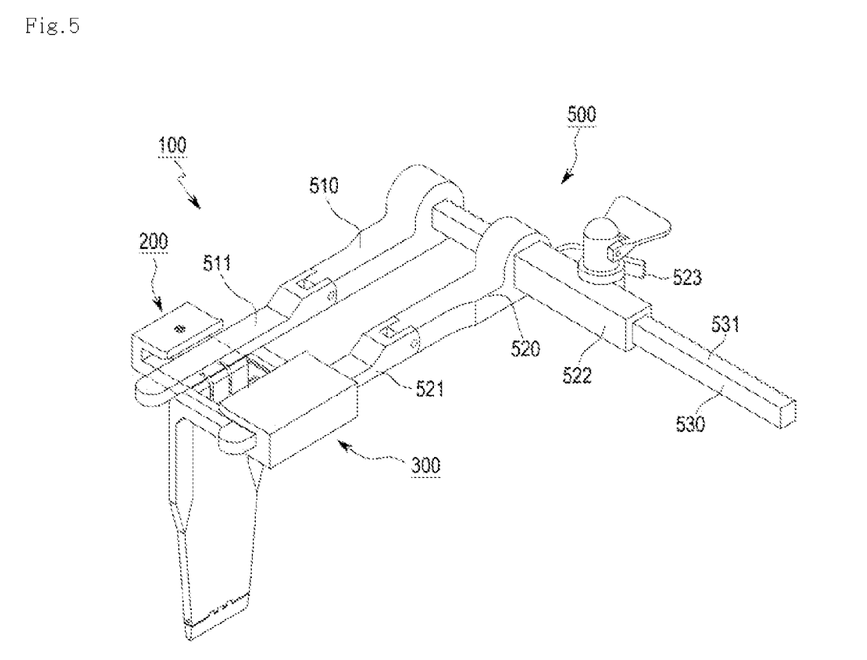
FIG. 5 is a view showing a state in which an expander is installed at the retractors according to the present invention.
Figure 6:
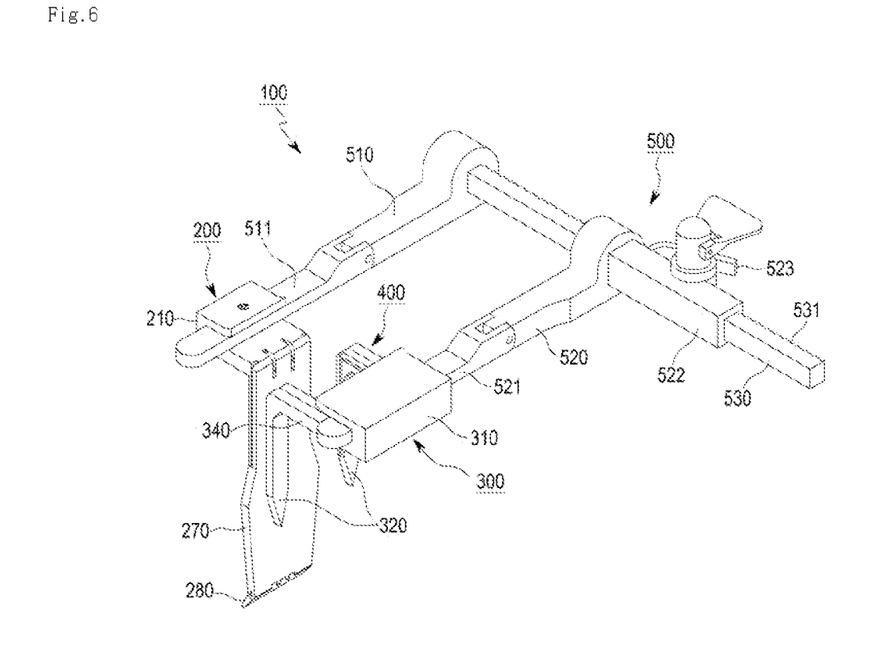
FIG. 6 is a view showing a state in which the retractors according to the present invention are expanded by the expander.
Figure 7:
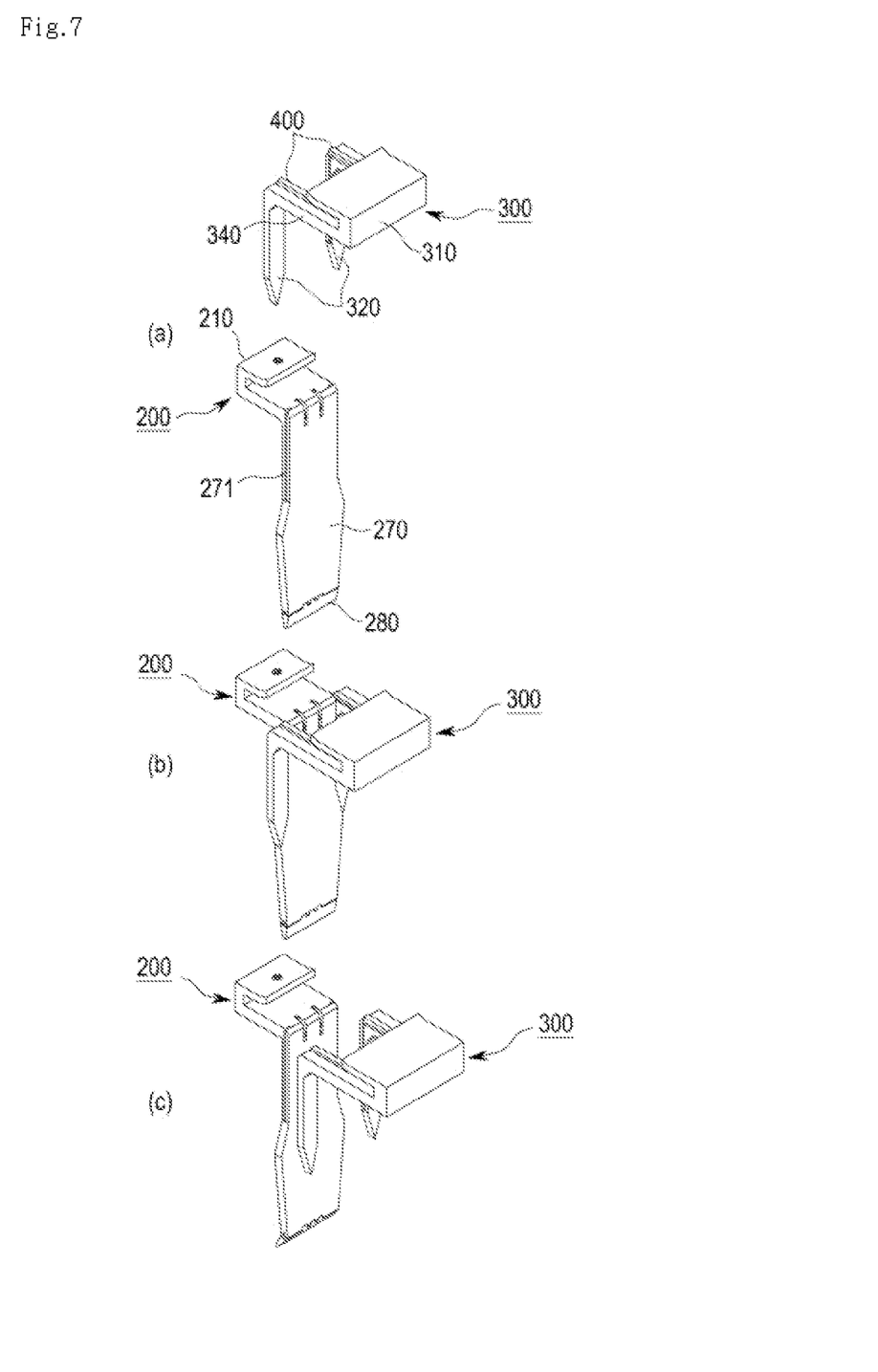
FIG. 7 is a configuration view of the retractors according to the present invention, FIG. 7(a) showing a coupling process of both of the retractors, FIG. 7(b) showing a coupling stage of both of the retractors, and FIG. 7(c) showing a state in which both of the retractors are expanded and separated from each other.

As shown in FIGS. 5 and 6, the expander 500 is an apparatus for releasing the locking state of the first and second retractors 200 and 300 and spreading and expanding the first and second retractors 200 and 300.

The expander 500 includes the first and second expansion arms 511 and 521 inserted into the first and second insertion blocks 210 and 310 of the first and second retractors 200 and 300 to expand the first and second retractors 200 and 300, first and second spreaders 510 and 520 hinged to one ends of the first and second expansion arms 511 and 521, a gear rack 530 movably installed at one ends of the first and second spreaders 510 and 520 and having a gear section 531 formed at one surface thereof, and a ratchet 523 installed at the expansion arm moving along the gear rack 530 to be locked by or released from the gear section 531 of the gear rack 530.

The expansion arms 511 and 521 hinged to the ends of the first and second spreaders 510 and 520 can maintain a curved shape conforming to the curved shape of the expander 500 or the like during the surgery.

In addition, while both of the first and second spreaders 510 and 520 can move along the gear rack 530, in the embodiment, the first spreader 510 is configured to maintain a state fixed to one end of the gear rack 530, and the second spreader 520 is configured to move along the gear rack 530 and be fixed to the gear rack 530 by the ratchet 523.

Accordingly, the ratchet 523 is installed on the second spreader 520m which is movable. More preferably, a hollow movable tubular body 522 is integrally formed with one end of the second spreader 520, the gear rack 530 is movably installed to pass through the movable tubular body 522, and the ratchet 523 is resiliently pivotally installed at the movable tubular body 522, so that one end of the ratchet 523 is locked to or released from the gear section 531 of the gear rack 530.

In addition, while not shown in the embodiment, a pinion gear meshed with the gear section 531 of the gear rack 530 may be installed at the movable tubular body 522, and the second spreader 520 may finely move on the gear rack 530 according to rotation of the pinion gear, finely adjusting movement of the second spreader 520. Of course, here, the ratchet 523 may be latched to the pinion gear.

An operation of the muscle retractor for spine surgery according to the present invention will be described.

First, the first and second retractors 200 and 300 are coupled to each other through the slider 400 and then installed at an incised area of a patient for spine surgery.

That is, in a state in which the insertion blocks 210 and 310 of the first and second retractors 200 and 300 are seated on an outer surface of the back of the patient, the blades 270 and 320 of the first and second retractors 200 and 300 are installed between the muscles and spinous process of the spine. Here, since the blades 270 and 320 are integrally coupled to each other, the blades 270 and 320 can be easily inserted therebetween.

In this state, the expansion arms 511 and 521 installed at the first and second spreaders 510 and 520 of the expander 500 are seated on a bottom surface of the first insertion block 210 of the first retractor 200 and the extension section 340 of the second retractor 300, respectively.

Here, when the second expansion arm 521 of the second spreader 520 is seated on the extension section 340 of the second retractor 300, the slider 400 protruding over the extension section 340 is pressed and lowered by the second expansion arm 521 of the second spreader 520.

In addition, the slider 400, which is lowered as described above, is lowered diagonally, not vertically, by the inclined groove 322 formed in the side surface groove 321 of the support blade 320 and the inclined protrusion 421 of the slider 400, the horizontal section 410 of the slider 400 is inserted into the stepped section 341 of the extension section 340, and the vertical section 420 of the slider 400 is inserted into the side surface groove 321 of the support blade 320.

Accordingly, as the slider 400 is completely inserted into the stepped section 341 and the side surface groove 321 as described above, the first retractor 200 locked by the projected portion of the slider 400 is released from the second retractor 300 to become separable.

In this state, as shown in FIG. 5, the expander 500 is moved toward the second retractor 300 to lock the second expansion arm 521 of the second spreader 520 into the second insertion block 310 of the second retractor 300, the ratchet 523 is released from the gear section 531 of the gear rack 530 to move the first spreader 510 and the gear rack 530 away from the second spreader 520, and then the first spreader 510 is moved until the first expansion arm 511 comes in contact with the inside of the first insertion block 210 of the first retractor 200. Here, the expansion arms 511 and 521 can be easily inserted into the insertion blocks 210 and 310 by the curved ends 211 and 311 formed by the first and second insertion blocks 210 and 310, respectively.

Meanwhile, as show in FIG. 8, when the first expansion arm 511 of the first spreader 510 is inserted into the first insertion block 210 of the first retractor 200, one end of the pivot plate 220 is pivoted upward from the moment that the projection 222 of the pivot plate 220 installed at an inner upper surface of the first insertion block 210 comes in contact with the first expansion arm 511.

Accordingly, the latching protrusion 231 latched by the latching groove 221 of the pivot plate 220 is released from the latching groove 221, and the movable block 230 becomes movable. When the first expansion arm 511 of the first spreader 510 inserted into the first insertion block 210 comes in contact with one surface of the movable block 230 to move the movable block 230, the movable block 230 further enters the first insertion block 210.

Then, the first link 240 straightly pulls the movable block 230 by the movable block 230 moved as described above, the pivot link 250 is pivoted counterclockwise about the pivot shaft 251 by the first link 240, and the second link 260 is pulled upward to pivot the auxiliary plate 280 upward by pivotal movement of the pivot link 250 (see a right drawing of FIG. 8).

The auxiliary plate 280 pivoted as described above is pivoted at the lower end of the retraction blade 270 to an angle of 25 to 30 degrees to securely surround and grip the muscles.

In this state, when the first spreader 510 and the gear rack 530 are further pushed and moved, as shown in FIG. 6, the first retractor 200 is moved with the first spreader 510 and the retraction blade 270 of the first retractor 200 moves while surrounding the muscles. In a state in which the support blade 320 of the second retractor 300 comes in contact with and is supported by the spine, the spine and the muscles therearound of the affected area incised by the first and second retractors 200 and 300 are widened and expanded so that an operator can secure a sufficient view and surgical space.

As described above, in the muscle retractor for spine surgery of the present invention, as the first and second retractors are coupled and spread by the expander, the second retractor supports the spine and the plate-shaped retraction blade of the first retractor uniformly pulls and retracts the muscles around the spine from the spine, providing a surgical space appropriate for hemilaminectomy, which is performed relatively often in spine surgery.

More specifically, the retraction blade is inserted into the muscles in a flat shape upon insertion into the muscles, and then the auxiliary plate of the end thereof is pivoted to surround and grip the muscles. Accordingly, the retraction blade can be smoothly inserted between the muscles to securely grip and retract the muscles.

In addition, according to the present invention, since the blade and the retractor are slid and coupled to each other sideways, the blade need not be raised during the coupling process, and the muscles gripped by the blades can be prevented from being separated from the blades during the coupling process.

Further, according to the present invention, as the two blades are inserted between the muscles in a state in which the blades are integrated through the reactors, cumbersomeness and inconvenience generated during insertion of the blades can be removed.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A muscle retractor for spine surgery for retracting muscles from a spine, comprising:
    a first refractor having a first blade and a first insertion block extending from the first blade, the first blade having first side surfaces formed with a first side groove;
    a second retractor having a pair of second blades and a second insertion block extending from the second blades, each second blade having second side surfaces, one of the second side surfaces having a second side groove,
    wherein the first and second retractors are configured to support the spine and the muscles,
    wherein each of the first and second insertion blocks has an open surface;
    an expander having first and second expansion arms slidably inserted into the first and second insertion blocks to expand the first and second retractors, a gear rack movably installed at the first and the second expansion arms and having a gear section formed at one surface thereof, and a ratchet installed at the second expansion arm moving along the gear rack and locked to or released from the gear section of the gear rack;
    a slider, one end of the slider accessibly inserted into the first side groove and the other end of the slider accessibly inserted into the second side groove in a projected state and configured to restrict or release the first retractor or the second retractor; and
    an auxiliary plate pivotally installed at a lower portion of the first blade, and pivoted according to insertion of the first expansion arm of the expander into the first insertion block.

2. The muscle retractor for spine surgery according to claim 1, wherein a downwardly inclined groove is formed in the first and the second side surface grooves into which the slider is accessibly inserted,
    an inclined protrusion inserted into the inclined groove protrudes from the slider, and
    a resilient member configured to resiliently support the inclined protrusion is installed between the inclined groove and the inclined protrusion.

3. The muscle retractor for spine surgery according to claim 1, wherein a pivot unit of the auxiliary plate comprises:
    a pivot plate pivoted according to insertion of the first expansion arm of the expander into an inner side surface of the first insertion block;
    a movable block locked by the pivot plate and movable in the first insertion block by the first expansion arm as the locking is released upon pivotal movement of the pivot plate;
    a first link pivotally coupled to and interlocked with the movable block;
    a pivot link pivotally coupled to the first link and interlocked and pivoted about a pivot shaft of the first retractor by the first link; and
    a second link pivotally coupled to the pivot link and connected to the auxiliary plate to pivot the auxiliary plate in a forward or rearward direction.

4. The muscle retractor for spine surgery according to claim 3, wherein a projection configured to come in contact with the first expansion arm inserted into the insertion block and pivot the pivot plate protrudes from a lower surface of the pivot plate, and
    a resilient member is installed at an inner side surface of the insertion block on the pivot plate, and a support member is resiliently supported by the resilient member and comes in contact with an upper surface of the pivot plate to return the pivot plate to its original state.

* * * * *